US009796587B2

(12) United States Patent
Cole et al.

(10) Patent No.: US 9,796,587 B2
(45) Date of Patent: Oct. 24, 2017

(54) SYSTEM AND METHOD FOR PRODUCING A CONSISTENT QUALITY SYNGAS FROM DIVERSE WASTE MATERIALS WITH HEAT RECOVERY BASED POWER GENERATION, AND RENEWABLE HYDROGEN CO-PRODUCTION

(71) Applicant: Renewable Opportunities Inc., Tinton Falls, NJ (US)

(72) Inventors: Randall Cole, Albany, NY (US); Seth Murphy, Tinton Falls, NJ (US); Ronald Bruer, Reston, VA (US); Edmund Kaminski, Holly Springs, NC (US); Peter Sach, Fair Haven, NJ (US)

(73) Assignee: Renewable Opportunities Inc., Tinton Falls, NJ (US)

( * ) Notice: Subject to any disclaimer, the term of this patent is extended or adjusted under 35 U.S.C. 154(b) by 78 days.

(21) Appl. No.: 15/012,918

(22) Filed: Feb. 2, 2016

(65) Prior Publication Data
US 2016/0145098 A1    May 26, 2016

Related U.S. Application Data

(63) Continuation of application No. 14/216,692, filed on Mar. 17, 2014, now Pat. No. 9,315,735.

(51) Int. Cl.
*C10B 49/14* (2006.01)
*C10J 3/57* (2006.01)
(Continued)

(52) U.S. Cl.
CPC ............... *C01B 3/32* (2013.01); *C01B 3/342* (2013.01); *C01B 3/348* (2013.01); *C07C 29/1518* (2013.01); *C10G 2/30* (2013.01); *C10G 2/32* (2013.01); *C10L 1/04* (2013.01); *C10L 3/08* (2013.01); *C12P 5/023* (2013.01); *C01B 2203/04* (2013.01); *C01B 2203/0405* (2013.01); *C01B 2203/0415* (2013.01); *C01B 2203/0465* (2013.01); *C01B 2203/061* (2013.01); *C01B 2203/062* (2013.01); *C01B 2203/0833* (2013.01); *C01B 2203/0861* (2013.01); *C01B 2203/142* (2013.01); *C10L 2290/04* (2013.01); *C10L 2290/26* (2013.01); *C10L 2290/38* (2013.01); *C10L 2290/42* (2013.01); *C10L 2290/547* (2013.01); *Y02E 20/18* (2013.01);
(Continued)

(58) Field of Classification Search
CPC combination set(s) only.
See application file for complete search history.

(56) References Cited

U.S. PATENT DOCUMENTS

2003/0130360 A1*  7/2003  Kindig ................ B01J 7/00
                                                      518/703

* cited by examiner

*Primary Examiner* — Kaity Chandler
(74) *Attorney, Agent, or Firm* — Chi Eng

(57) ABSTRACT

A system and method for converting waste and secondary materials into synthesis gas (syngas) through the use of a molten metal bath gasifier for the initial breakdown of waste feeds and an A/C plasma reactor for complete dissociation of waste feeds into syngas, and an anaerobic digester. The system includes a heat recovery and steam power generation process for the production of electricity. The system produces a net output of electricity above plant load sufficient for the co-production of renewable Hydrogen and Oxygen. The process does not require the use of fossil fuels or fossil feedstocks during normal operations, and it eliminates combustion produced stack emissions or landfill residuals.

23 Claims, 3 Drawing Sheets

(51) Int. Cl.
    *B01J 7/00*         (2006.01)
    *C01B 3/32*        (2006.01)
    *C10L 3/08*        (2006.01)
    *C10G 2/00*       (2006.01)
    *C01B 3/34*        (2006.01)
    *C07C 29/151*     (2006.01)
    *C10L 1/04*        (2006.01)
    *C12P 5/02*        (2006.01)

(52) U.S. Cl.
    CPC ............... *Y02E 50/13* (2013.01); *Y02E 50/18* (2013.01); *Y02E 50/343* (2013.01); *Y02P 30/10* (2015.11)

SYSTEM AND METHOD FOR PRODUCING A CONSISTENT QUALITY SYNGAS FROM DIVERSE WASTE MATERIALS WITH HEAT RECOVERY BASED POWER GENERATION, AND RENEWABLE HYDROGEN CO-PRODUCTION

RELATED APPLICATIONS

This is a continuation application of U.S. application Ser. No. 14/216,692 filed on Mar. 17, 2014, which claims priority from U.S. Provisional Patent Application Ser. No. 61/794,471 filed on Mar. 15, 2013.

BACKGROUND

The beneficial reuse of waste materials has long been a priority in the protection of human health and the environment. More recently, attempts have been made to use a larger variety of waste as a manufacturing feedstock, primarily through the use of various gasification techniques.

In the United States, the use of gasification technologies for waste disposal has been attempted with varying degrees of success since the 1970s. One of the biggest barriers to the use of waste materials as a manufacturing feedstock is the diversity of the chemical composition, moisture content, and physical characteristics of waste materials. This diversity is compounded by the variations in waste material from location to location, as well as changes in the characteristics of waste over time. Unlike fossil-based feedstocks (e.g., natural gas, coal) that have fairly consistent chemical composition and physical characteristics from one location to the next, waste materials are inherently diverse making the quality of waste-derived products more difficult to achieve.

The most common methods used to overcome the problems of waste diversity involve sorting; separating; mixing; or a combination of the three. Sorting and separating provides value in identifying wastes that have high energy value and desirable chemical compositions, but they are both capital and energy intensive, rendering the systems cost prohibitive. Mixing waste provides a less expensive method for homogenizing the waste from one batch to another, but the potential for undesirable chemical reactions increases risks to human health and the environment.

Synthesis gas (syngas) derived products, with integrated electric power co-generation using virgin fossil feedstocks and/or waste feedstocks, have been manufactured on an industrial scale since the mid-20$^{th}$ Century. It is a well understood practice that essentially involves the recycling of Carbon, Hydrogen and Oxygen at the molecular level and managing energy efficiencies in order to optimize the financial results for the systems' owners. Historically, this has meant that a portion of the syngas is combusted in an integrated gasification combined cycle (IGCC) system to increase net power production, at the expense of stack emissions. Given the current realities of the national energy security situation, there is an ever increasing demand for syngas-derived products made from domestic and renewable resources. However, there is opposing pressure from environmental protection priorities to reduce combustion stack emissions and greenhouse gas emissions.

The problem with conventional approaches is the persistence of an open-loop in the mass and energy balancing of the whole system. Zero-emissions can be achieved using conventional systems, but normally require an energy input in the form of pure Oxygen, natural gas (methane) or grid power. Even though this can theoretically be solved using 100% renewable energy, the financial sustainability of the system becomes questionable due to the cost of utilities.

SUMMARY OF THE INVENTION

An embodiment of the present invention overcomes the heterogeneity of waste issues by focusing on wastes of known composition (e.g., weight/volume; chemical composition) that are used as feedstocks. This is accomplished by focusing on Industrial Solid Waste which is manifested to comply with EPA and U.S. Department of Transportation (DOT) regulations, focusing on specific waste streams (e.g., waste from paint manufacturers), as well as other known waste products (secondary materials). This specific knowledge of the waste materials that are used as feedstocks allows the waste to be processed more effectively and safely.

According to an aspect of the invention, the inventive process comprises the following steps: (a) tagging (e.g., barcode, quick response code, radio frequency identification tag [RFID]) of feedstock materials at the source concurrent with manifesting for transportation; (b) electronic sharing of manifest information by all parties involved with generating, transporting, and beneficial reuse; (c) leveraging tagged/manifest data to maximize processing efficiency, as well as environmental health and safety, while minimizing the risks inherent in chemical and physical variation in 'unknown' feedstocks; (d) loading of pumpable non-biodegradable feedstocks into a filtration system to remove unwanted particulates; (e) loading of non-pumpable non-biodegradable feedstocks into mechanical processing equipment for size reduction without decanting or other removal from shipping containers; (f) loading of biodegradable feedstocks into separate mechanical processing systems; and (g) slurification.

According to another aspect of the invention, the process does not rely on any fossil fuels or fossil feedstocks to be consumed during normal operations, nor does it produce any environmentally harmful emissions or waste byproducts requiring landfill disposal or further treatment.

In one embodiment, the invention also manages the flow and mix of chemistry input into the system, without the physical pre-mixing of waste materials, through the processing of data and information about the materials in an over-arching operations control and monitoring system.

In addition, the invention employs a multi-stage process where biogas, from an anaerobic digester, preferably has an average methane ($CH_4$) content of about 75%. In gasification systems, biogas is typically used as a combustion fuel or as a commodity product. In this invention, biogas is counter-intuitively used as a waste feedstock to add energy to the system, as well as a working gas for the plasma generator.

In another embodiment, the invention captures the heat generated from the various processes to create steam which is used to generate electricity in amounts over and above processing requirements. Capturing a portion of the heat generated by the various processes employed in the invention eliminates the need for a combustion process to generate electricity with the associated smokestack and/or utility inputs during normal operating conditions.

According to yet another aspect of the invention, the process uses a molten metal bath gasifier (MMBG) to convert the non-biodegradable feedstocks into a raw process gas comprised mostly of Hydrogen ($H_2$) and carbon monoxide (CO), and an anaerobic digester to convert biodegradable feedstocks into a raw biogas comprised mostly of methane ($CH_4$) and carbon dioxide ($CO_2$).

While there are different MMBGs that can be used in the invention, a preferred embodiment is a MMBG with an iron bath operating between 1,150° C.-1,600° C. (the melting point range for various types of Iron). While molten iron is used in the preferred embodiment, it is contemplated that other metals may be used in the MMBG. Similarly, different types of anaerobic digesters can be used in the invention, but in a preferred embodiment a thermophilic anaerobic digester operating in a temperature range of 49° C.-57° C. is used. Using a thermophilic process with its higher temperature range (compared to a mesophilic process) provides the advantage of a higher energy yield and it facilitates greater sterilization of the digestate.

The raw process gas from the MMBG is conveyed to a thermal dissociation reactor wherein it is ionized by exposure to a plume from an alternating current (A/C) plasma generator hot enough to complete the molecular dissociation of the raw input gases. This produces a syngas comprised mostly of Hydrogen ($H_2$) and carbon monoxide (CO). The syngas is then cooled, cleaned (e.g., filtered) and conditioned as required for synthesis into methanol and/or other primary liquid product, or separated into its constituent industrial gas products.

The inventive process converts waste and secondary materials into syngas through the use of a MMBG and an A/C plasma reactor, integrated with an anaerobic digester. Solid phase materials are mechanically processed for size reduction to facilitate passage through equipment input ports. With limited exceptions, non-biodegradable materials are processed using the MMBG. Biomass and other biodegradable wastes are input into anaerobic digesters for the production of raw biogas. While liquid wastes and other pumpable materials are normally input into the MMBG for processing, they may be input directly into the A/C plasma reactor for streamlined processing, particularly when the MMBG is operating at capacity. In a preferred embodiment, the MMBG comprises an enclosed, refractory lined and jacketed vessel with multiple injection ports for feedstocks and the other normal process inputs required for managing the molten media and the internal environment of the vessel. The vessel also has normal metal and slag tapping systems. The MMBG smelts most metals and incorporates them into the molten bath. Feedstocks are injected into the melt and are instantly dissociated upon contact with the molten bath. The MMBG also melts silicates and others minerals which are impounded within a molten slag layer that floats on top of the molten metal. In this stage of the process, the metals and minerals are periodically recovered and processed into commodity products (e.g., pig iron and silicate slag). Everything else is converted into a dirty, raw process gas which is input into the A/C plasma reactor for further processing.

The use of a separate MMBG upstream from the A/C plasma reactor is counter-intuitive since it adds additional cost to the system. Further, molten baths and plasma generators are commonly used within the same vessel to gasify materials. The advantages of separating the melt from the plasma reactor include the ability to use the energy from the waste feedstocks to sustain the melt, reducing/eliminating the requirement to sustain the melt from external energy sources.

In a preferred embodiment, induction heating is used to establish the melt, after which it is maintained by the energy input from the waste feedstock. Using the melt as a process media in this manner, rather than just a heat sink as in other systems, offers several advantages:

(i) an efficient method for initial dissociation of materials due to its high operating temperatures compared to typical fixed bed, moving bed, fluidized bed or entrained flow gasifiers;

(ii) faster destruction and destruction rate efficiencies (DREs) compared to all lower temperature methods;

(iii) faster destruction and DRE compared to gasifiers wherein molecular dissociation occurs primarily in the atmosphere between the melt and the reactor ceiling, including traditional Direct Current (D/C) plasma-arc systems. Even though the temperature of the plasma arc itself can well exceed 7,900° C., the energy density of the atmosphere in the reactor vessel will be less than that of the molten media;

(iv) little or no charring of carbonaceous feedstocks, an undesirable reaction that among other things increases the energy needed for gasification, will occur when feedstocks are injected into the molten media. This enables an energy efficiency gain compared to processes wherein gasification occurs primarily in the atmosphere of the reactor vessel;

(v) the ability to scale the size of the MMBG and the plasma reactor independent of each other; and (vi) perhaps mostly importantly, use of the melt as working media rather than as a heat sink significantly improves the process and energy efficiency of downstream gas clean-up processes by impounding a significant amount of the contaminates inherent in the feedstocks within the molten media, and preventing their release and incorporation into the process gas stream.

In traditional gasification processes, the process gas would be conveyed directly to a series of heat recovery and syngas cleanup and conditioning systems. The present invention conveys the dirty process gas into an A/C plasma reactor to complete the molecular dissociation process.

The temperature of the plasma plume inside the A/C plasma reactor vessel can exceed 7,900° C. In this invention, all material input into the A/C plasma reactor is converted into a gaseous or plasma phase and then begin to condense into an extremely hot syngas. The output syngas is subsequently cooled and conditioned to remove contaminates leaving a clean mixture of Hydrogen ($H_2$) and carbon monoxide (CO).

Although either A/C or D/C plasma generators may be used, (both of which can generate plasmas with energy levels greater than 7,900° C.—the threshold at which no known molecule can survive), the A/C plasma generator is preferred due to its significant advantages over D/C plasma technologies; primarily in that it generates a wide plume of plasma that is better suited for dissociating a large volume of process gas compared to the relatively very narrow arc generated by a D/C plasma generator.

In addition, A/C plasma generators typically have a lower operating cost as they do not incur the cost of continuously consumed carbon electrodes as do D/C plasma generators. Moreover, the biogas from the anaerobic digestion process may also be used as the working gas for the A/C plasma generator as a non-utility source of additional energy for the system.

Exposure of the process gas from the MMBG to the high energy plasma plume created by ionizing the methane ($CH_4$)-rich biogas from the anaerobic digester induces complete molecular dissociation of all inputs, as well as a desirably higher ratio of Hydrogen ($H_2$) to carbon monoxide (CO) in the resulting syngas.

The anaerobic digester processes biomass and other biodegradable materials (predominately plant, animal, and food processing wastes) to produce a raw, methane-rich biogas. This biogas is used as an alternative to natural gas to increase the level of $H_2$ and to add additional energy to the system. It is injected into the MMBG, and/or into the A/C plasma reactor. It is also used as the working gas for the plasma generator. Agricultural grade solids (digestate) are recovered from the digesters on a periodic basis as a commodity product. Wastewater (effluent) is either recycled to add fluids (as needed) to the anaerobic digester or filtered and input into the MMBG for processing.

Multiple continuous feed anaerobic digestion process trains may be used to maximize uptime availability of the inventive system. The digestion process utilizes the bacterial hydrolysis, acidogenesis, and methanogenesis processes to convert biodegradable feedstocks into a biogas with an average methane ($CH_4$) content of 75%. The biogas is filtered to remove particulates before being input into the MMBG or the A/C plasma reactor.

One major byproduct of the digestion process is wastewater (effluent). When needed, the effluent is recycled into the anaerobic digestion process, reducing the demand for fresh water; and/or the effluent is filtered and beneficially re-used as a feedstock in the MMBG. Advantageously, the wastewater ($H_2O$), when used as a process feedstock, increases the ratio of $H_2$ to CO.

The other major byproduct of the digestion process is a nutrient rich bio-solid commonly known as digestate. The recovered digestate has significant commercial value as a fertilizer and/or a soil amendment product.

In one embodiment, the hot process gas from the A/C plasma reactor is rapidly cooled to prevent the reformation of tars, dioxins, furans, and other undesirable compounds. In the first quench, heat is stripped to lower the temperature to approximately 800° C. The gas is then very rapidly cooled through the 400° C. to 200° C. temperature window to prevent de novo formation of dioxins and furans. The final stage requires the syngas to be cooled below 38° C., the optimal temperature for the downstream cleanup systems.

Removal of contaminates from the syngas is achieved through a series of gas cleanup and conditioning systems including, but not limited to, high temperature cyclones, scrubbers, granulated activated charcoal (GAC) and other filters, and other membrane technologies, as well as selective and non-selective catalytic converters.

Syngas clean-up is also performed in a closed-loop manner, with "contaminates" (e.g., particulates, volatized metals, minerals and any acid gases that reform) extracted as commercially valuable "recovered resources". For example:

(i) Chlorine is removed as either hydrochloric acid (HCl), an important industrial product, or as sodium chloride (NaCl), commonly known as "salt" via reaction with sodium hydroxide (NaOH), (ii) Elemental Mercury, Lead and other metals that may have volatized and blown through with the process gas are extracted in industrial grade forms; and (iii) Sulfur that was not impounded within the melt or slag is also extracted in a commercially valuable elemental or compound form.

The clean syngas can then be conditioned to meet the input requirements of any number of catalytic conversion processes to produce a value-added product such as methanol; Fischer-Tropsch (F-T) Synfuel; etc.

Various stages of this process produce large quantities of heat from exothermic processes or reactions. In particular, heat generated from the MMBG, the plasma reactor, the anaerobic digester, the syngas cooling system, and the product recovery processes (when appropriate) is recovered through a combination of thermal wraps, radiators, jacketing and other heat exchangers. The recovered heat is used to produce pressurized steam to power a steam turbine plant for the production of electricity. The system is designed to enable the production of electricity over and above plant load to eliminate the dependence on grid power during normal operating conditions. The excess electricity is used to dissociate water into commodity $H_2$ and $O_2$ gas products via an electrolysis process.

Furthermore, given the energy inputs from multiple sources (including the energy contained in the molecular bonds of the feedstocks; the biogas from the anaerobic digester; and the integral exothermic processes), there are numerous mass-energy balance scenarios wherein sufficient heat energy can be recaptured to generate enough electricity via steam turbine to meet and/or exceed the energy load of the plant during normal operating conditions. This eliminates the need to combust any portion of the syngas as a fuel in an IGCC turbine, and the open-loop stack emissions inherent with any combustion process.

According to another aspect of the invention, the entire inventive process is monitored and controlled through an integrated computerized system. Commercially available sensory, monitoring and control systems are used to manage the components of the system and the flow of matter through the system. While these systems function as stand-alone monitor and control systems for the discrete elements to which they are attached, all of these systems are integrated into one overarching monitor and control system allowing end-to-end management of the entire process.

Under normal operations the process does not require the use of fossil fuels or fossil feedstocks. In addition, the process does not rely on any combustion processes that would result in greenhouse gases being released into the atmosphere. Under normal operating conditions the process emits Oxygen ($O_2$), Nitrogen ($N_2$) and trace amounts of other elements (e.g., Argon), all of which are naturally occurring, non-harmful atmospheric elements. During some maintenance procedures wastewater is generated which is suitable for processing in any publicly owned treatment works (POTW) or it can be reprocessed in the MMBG.

The products recovered from the inventive process are highly beneficial to numerous industrial processes. For example, syngas is commonly used as the feedstock in a number of catalysis processes to produce a wide range of industrial, commercial and consumer products. Methanol synthesis is one of the simplest, most well understood and easily implemented processes from a technical standpoint, and one of the most environmentally and economically sustainable. In 2011, the U.S. methanol demand was approximately 5.7 million metric tons, or about 1.9 billion gallons per year. The majority of methanol is made via steam reforming of natural gas (with syngas as the intermediary). About 60% of all methanol is used in the production of formaldehyde and acetic acid, both precursors to numerous adhesives, glues, plastics and other materials. Other major uses include solvents, antifreeze, and windshield washer fluid. Methanol can also be converted into hexane—the primary constituent of motor gasoline. It is also a critical feedstock in the production of BioDiesel.

The process of the invention will support the syngas input requirements of all commercial methanol synthesizers (and ancillary systems) to produce methanol that conforms to International Methanol Producers & Consumers Association (IMPCA) specifications. Methanol synthesis is an exothermic reaction and heat recovered can also be used to augment steam generation for the production of electricity.

The inventive process also supports the syngas input requirements of other product recovery platforms including F-T synthesizers used to manufacture synthetic fuels. Non-productizable fractions of F-T process outputs can be reused as process feedstocks preserving the closed-loop configuration.

According to the present invention, the system and process for efficiently converting heterogeneous waste materials (biodegradable, non-biodegradable, and secondary wastes) into a high quality syngas comprises the following aspects:

(a) a first subsystem for inputting and filtering pumpable non-biodegradable waste;

(b) a second subsystem for inputting and resizing non-pumpable, non-biodegradable waste;

(c) a third subsystem for inputting, resizing, and slurification (as necessary) for biodegradable waste;

(d) a molten metal bath gasifier (MMBG), preferably using an iron bath, operating between 1,150° C.-1,600° C.;

(e) an anaerobic digester, upstream from the MMBG, (preferably a thermophilic anaerobic digester, operating in a temperature range of 49° C.-57° C.);

(f) an A/C plasma reactor (preferably with the plasma plume aimed or oriented upward);

(g) waste materials in (a) and (b) excludes: Universal Wastes (40 CFR 273); explosives and munitions; concentrated halogens; and heavy metals;

(h) the MMBG is placed upstream from the A/C plasma reactor;

(i) the biogas generated from the anaerobic digester is used as both a waste feedstock (input to either the MMBG, the A/C reactor, or both; as well as a working gas for the A/C plasma generator, where, in the preferred embodiment, the biogas has an average composition 75% $CH_4$; 18% $CO_2$; 1% $N_2$; 5% $H_2O$, and 1% $O_2$ and other trace elements ($H_2S$ and $NH_3$);

(j) filtered pumpable liquids may be input directly into the A/C plasma reactor, for increased processing capacity;

(k) waste products from various filtration processes (102; 142; 146; 160) can be input back into the system (130) as a feedstock;

(l) where the entire system is closed-loop, with the exception of the venting of Oxygen ($O_2$), Nitrogen ($N_2$) and trace amounts of other elements (e.g., Argon), all of which are naturally occurring, non-harmful atmospheric elements;

(m) the heat generated by five primary subsystems (130; 140; 150; 160; 170) is recovered with heat exchangers, pumped to a Heat Recovery Steam Generation Utility, which creates steam to drive a steam turbine, which in turn generates electricity;

(n) the production of electricity is produced in quantities over and above plant load requirements;

(o) the excess electricity is used to dissociate water into commodity $H_2$ and $O_2$ gas products via an electrolysis process;

(p) the hot process gas from the A/C plasma reactor is rapidly cooled to prevent the reformation of tars, dioxins, furans, and other undesirable compounds. In the first quench, heat is stripped to lower the temperature to approximately 800° C. The gas is then very rapidly cooled through the 400° C. to 200° C. temperature window to prevent de novo formation of dioxins and furans. The final stage requires the syngas to be cooled below 38° C., the optimal temperature for the downstream cleanup systems;

(q) the syngas contaminates are removed in a closed-loop manner through a series of gas cleanup and conditioning systems including, but not limited to, high temperature cyclones, scrubbers, granulated activated charcoal (GAC) and other filters, and other membrane technologies, as well as selective and non-selective catalytic converters; commercially valuable volatized metals and minerals are recovered, and non-commercial by-products are used as a waste feedstock for the MMBG;

(r) syngas clean-up is also performed in a closed-loop manner, with 'contaminates' (e.g., particulates, volatized metals, minerals and any acid gases that reform) extracted as commercially valuable 'recovered resources';

where Chlorine is removed as either hydrochloric acid (HCl), an important industrial product, or as sodium chloride (NaCl), commonly known as "salt" via reaction with sodium hydroxide (NaOH), where Elemental Mercury, Lead and other metals that may have volatized and blown through with the process gas are extracted in industrial grade forms;

where Sulfur that was not impounded within the melt or slag is also extracted in a commercially valuable elemental or compound form;

(s) the clean syngas can then be conditioned to meet the input requirements of any number of catalytic conversion processes to produce a value-added product such as methanol; Fischer-Tropsch (F-T) Synfuel;

(t) the type and amount of feedstocks entered in the system are known (via electronic code, e.g., barcode, Quick Response Code, RFID, etc.);

(u) the entire system's operating parameters (minimum of 21 independent monitoring and control systems) are controlled and managed by an integrated Command/Control Management System;

(v) the energy in the system is monitored and adjusted (by controlling the type, quantity, and quality of feedstocks) to maintain operating levels sufficient to generate required amounts of electricity (see (n) above);

(w) electricity is used to dissociate water liquid or steam to produce commodities of Hydrogen ($H_2$) and Oxygen ($O_2$).

Advantages of the inventive system include:

1. MMBG is separate and upstream of the A/C plasma reactor to:
    a. Provide better thermal energy management;
    b. Enable the system to use energy from the waste feedstocks to sustain the melt, thereby reducing or eliminating the requirement to sustain the melt from external energy sources;
    c. Enable the system to scale the size of the MMBG and the A/C plasma reactor independent of each other;
    d. Use the melt as working media rather than as a heat sink to impound a significant amount of the contaminates (inherent in waste feedstocks) within the molten media, and preventing their release and incorporation into the process gas stream, thereby resulting in improved process and energy efficiency of downstream gas clean-up processes;

2. Biogas from the anaerobic digester is used as a waste feedstock and/or a process gas for the A/C plasma reactor.

3. All wastes created by the system are reprocessed as a feedstock back into the MMBG or A/C plasma reactor:
    a. Solid phase material goes into the MMBG;
    b. All other wastes go into either the MMBG or the A/C plasma reactor.

4. Composition of feedstock is known prior to being input into the system.

5. Heat is recovered from all heat-generating elements and used to create steam and then electricity to reduce the operating cost of the system by generating its own electrical power.

6. The entire system is managed by an integrated Command/Control Management System to:
   a. Allow control of the type and amount of feedstocks entering the system;
   b. Allow control of the system components to adjust operation parameters to accommodate heterogeneity of waste material; and
   c. Allow for off-site monitoring of the system.

7. The entire system is closed-loop, without producing combustion, greenhouse gas emissions, or landfill residuals.

DETAILED DESCRIPTION OF THE PRESENTLY PREFERRED EMBODIMENTS

Figure 1:
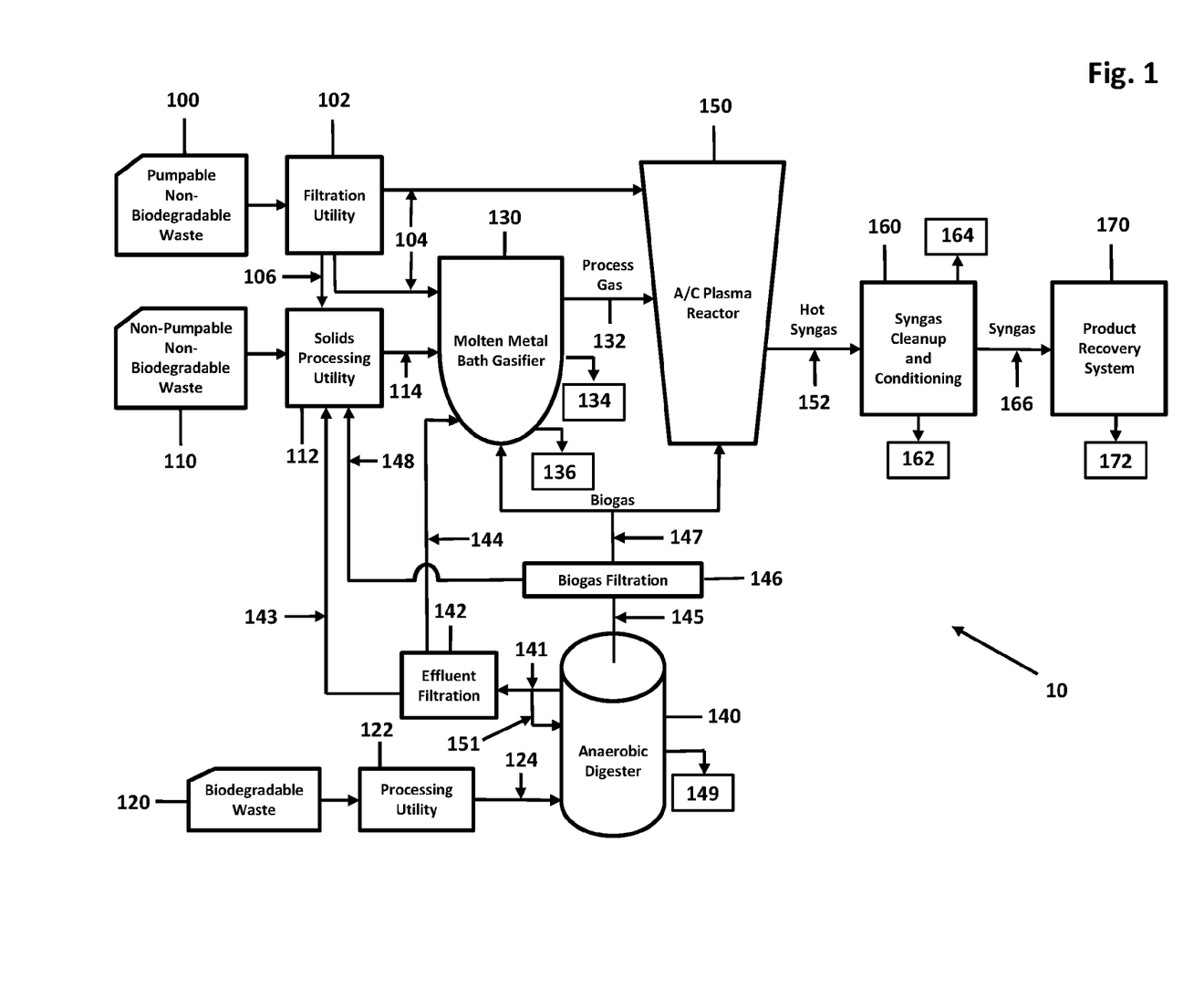
FIG. 1 is a flow diagram illustrating the preferred embodiment of the mechanical system for converting diverse waste materials into a consistent quality syngas (that can be further processed into other commodity products (e.g., methanol, synthetic fuels).

Referring now to FIG. 1, the presently preferred embodiment of the inventive system 10 begins with the acceptance of heterogeneous waste materials 100, 110, 120, which exclude, for example, Universal Wastes (see 40 CFR 273); explosives and munitions; radioactive materials; concentrated halogens and heavy metals. Waste products 100, 110, 120 received are identified (via electronic code, e.g., barcode, Quick Response Code, RFID, etc.) manually separated into three major categories for initial processing: 1) pumpable non-biodegradables 100; 2) non-pumpable solid/semi-solid materials, and any other non-liquid waste or secondary materials 110; and 3) biodegradables (e.g., plant, animal, and/or food industry waste) 120.

Biodegradable waste 120 is mechanically processed (shredding, grinding, milling, or other size reduction processes) by a biodegradables waste processing utility 122 to which water or other liquids are added as needed to produce a pumpable slurry 124 for input into a biogas generating system such as an Anaerobic Digester 140. In the preferred embodiment, one or more continuous multi-stage, thermophilic anaerobic digesters are used. It is contemplated that one or more mesophilic anaerobic digesters may be used in combination with the thermophilic digesters such as, for example, in a parallel arrangement.

Pumpable non-biodegradable waste 100 is strained and filtered 102 through screens to meet the requirements of injectors used to input liquids into the system. If the strained liquid material 104 contains more than trace amounts of phosphorus, magnesium, or any other potentially highly reactive element, it must be input into the molten metal bath gasifier (MMBG) 130 for processing. Otherwise the liquid material 104 may be input directly into either the MMBG 130 or the A/C plasma reactor 150. Residual material larger than the required size for the injectors 106 is recovered and input into the solids processing utility 112 for processing as a non-pumpable, non-biodegradable waste 110.

Non-pumpable non-biodegradable waste 110 is processed by the Solid Waste Processing Utility 112 to reduce the size of solid materials to a size ranging from 0.5" and 4.0" (typical size range for commercial size-reduction equipment) for efficient processing of the waste. It should be noted that larger sized waste material can be processed; however, processing efficiencies will be degraded (i.e., greater energy will be required for processing and the initial gasification process may not be uniform). Processing includes cutting, grinding, shredding, milling or other size reduction processes. Decanting of containerized waste is not required, as the system will process both the waste and the container. Following size reduction, the material 114 is input into the MMBG 130.

Input of waste material into the MMBG 130 serves as the first step in the syngas production process. Several metals will suffice for the molten bath, but iron is used in the preferred embodiment due to its abundant availability and its high melting point, thus allowing it to efficiently process a wide variety of diverse waste materials safely and efficiently.

Preferably, all materials are injected into the molten metal layer instead of the atmosphere of the MMBG 130. An objective is to reduce the amount of time material is exposed to the atmosphere at the top of the containment vessel of the MMBG 130 in order to reduce the creation of char. In the preferred embodiment, input tubes, channels, and injectors are angled downward and placed close to the level of the metal bath (above the slag layer). The material enters the MMBG 130 under pressure through the use of gravity, steam, pneumatic or mechanical force. Tubes, injectors, and/or channels placed inside the MMBG 130 are protected using refractory or other heat shielding material, or jacketing (heat exchanger) system.

While a variety of MMBGs can be used, a preferred embodiment uses a MMBG with a molten iron bath operating within a temperature range of 1,150° C.-1,600° C. When materials are input into the melt, the syngas production process begins. The energy content of the inputs is sufficient to maintain the molten state. Metals with a higher boiling point than the melting point of iron will smelt and become incorporated into the metal bath. The metal bath is periodically tapped and a commodity pig iron 136 is recovered. Minerals that melt, but do not volatize, rise to the top of the molten bath and form a slag layer which is periodically recovered as silicate glass 134. The gases formed, i.e. (process gas) 132, rise to the top of the reactor vessel and are input into the A/C plasma reactor 150 for further processing.

Figure 2:
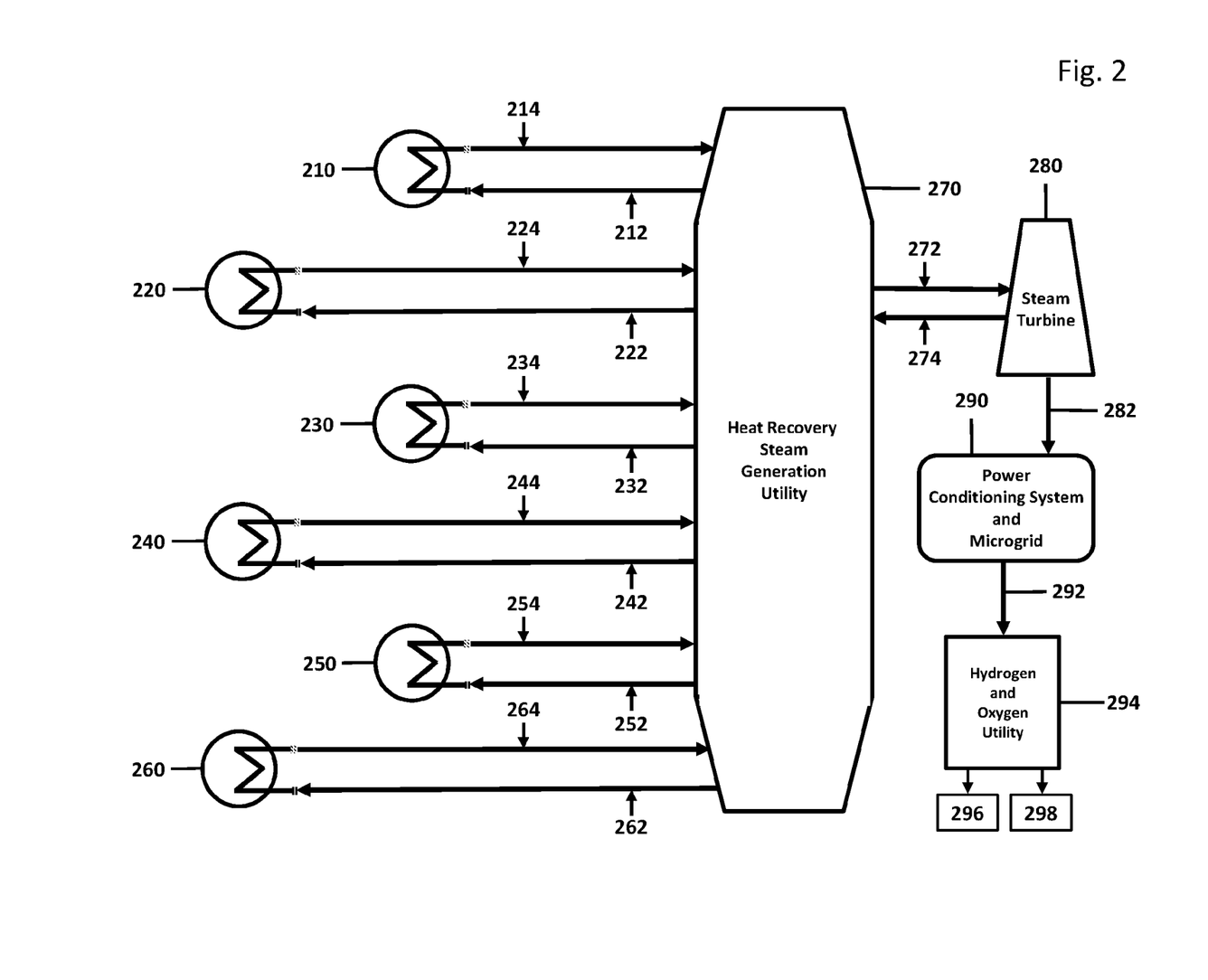
FIG. 2 is a flow diagram illustrating the preferred embodiment of the system for the recovery of heat and the conversion into steam to serve as a source of power to drive a generator to produce electricity.

The MMBG 130 has multiple input ports and diverse materials are dissociated immediately upon exposure to the molten iron before they can react (adversely) with other waste inputs, allowing a diversity of waste materials to be processed. Furthermore, the molten metal bath is an efficient method for capturing the energy released from the dissociation of the materials and transferring that heat to the heat recovery steam generation system 200 as shown in FIG. 2. In addition, the MMBG 130 is an efficient apparatus for processing waste streams from other processes in the system (i.e., filtration systems 102; 142; 146), supporting the closed-loop processing environment and eliminating the need for emissions.

The primary role of the anaerobic digester 140 is for the production of biogas. On average, the composition of the biogas from anaerobic digester is about 75% $CH_4$; 18% $CO_2$; 1% $N_2$; 5% $H_2O$, and 1% $O_2$ and other trace elements ($H_2S$ and $NH_3$). The biogas from the Anaerobic Digester 145 is processed and filtered by the Biogas Filtration 146 to remove acids, corrosives, or solid particulates which are typically produced in biogas production via anaerobic digestion, but which may degrade or impede processing by the MMBG 130 and/or the A/C plasma reactor 150. The filtered biogas 147 is then input into the MMBG 130 and/or A/C plasma reactor 150. Waste generated from the Biogas Filtration 146 is input into the solids processing utility 112 for processing in the system. The clean biogas 147 from Biogas Filtration 146 is used as an input feedstock for the MMBG 130 and the A/C plasma reactor 150. The biogas serves as an alternative to natural gas to increase the energy level of the system, generating heat which is recovered to create steam and generate electricity (see FIG. 2). It is also used as a working gas for the A/C plasma reactor 150.

Wastewater (effluent) 141 is periodically recovered from the anaerobic digester 140 and recycled 151 to add fluids to the anaerobic digester and/or filtered by Effluent Filtration 142 for further processing. The filtered wastewater 144 is input into the MMBG 130, adding stoichiometric amounts of $H_2$ and $O_2$ into the system. The residual material 143 from Effluent Filtration 142 is input into the Solid Waste Processing Utility 112 for processing. Agricultural grade solids (digestate) 149 are periodically recovered as a commodity product.

The A/C plasma reactor 150 is used to complete the dissociation process of the gas derived from the MMBG 130. Instead of aiming the plasma plume downward (as is the typical configuration in plasma gasifiers which use a plasma plume or plasma arc to dissociate solids and provide heat to an integrated metal bath), the plasma plume in the A/C plasma reactor 150 is advantageously aimed upward. Since no solid materials are injected into the plasma reactor (only gases and the occasional liquids), there is no need for a molten bath to entrap residual elements at this point in the process. All material input into the plasma reactor 150 dissociate and reach a plasma state. As this material reaches the top of the reactor, it cools to a gaseous state, forming hot syngas 152, which is input into a syngas cooling, cleanup, and conditioning system 160. Advantageously, configuring and using the plasma reactor 150 in this manner requires less energy to operate than a conventionally configured plasma gasifier that is used to dissociate solid materials and provide heat for a molten metal bath.

During the syngas cleanup and conditioning process in the Syngas Cleanup and Condition system 160, elements (e.g., Mercury, Lead, Chlorine, Sulfur) are filtered and removed to form a clean (contaminant free), high-quality syngas 166. The removed elements 162 are recovered as commodity products using commercial equipment and processes. During this phase, Oxygen ($O_2$) and Nitrogen ($N_2$) 164 are vented into the atmosphere, unless one or both elements are recovered as commodity products. If vented, these elements are commonly found in the atmosphere and are neither undesirable nor considered to be pollutants.

The clean syngas 166 is ready for further processing, which is achieved in the Product Recovery System 170 through catalytic conversion processes that are well understood by those knowledgeable in the art. The recovered products include methanol, and synthetic crude which can be refined into a variety of synthetic fuels (e.g., diesel, and jet fuels).

In this inventive system, several processes are exothermic and heat generated by these processes is recovered to create steam to generate electricity (FIG. 2). The generated electricity 282 is produced in amounts above and beyond the requirements needed to power all of the system processes (see energy balance equation below). The electricity 282 is conditioned by a Power Conditioning System and Microgrid 290, and a portion of the conditioned electricity 292 is used to dissociate water (liquid or steam) in a utility 294 to produce commodities Hydrogen ($H_2$) 296 and Oxygen ($O_2$) 298.

In the preferred embodiment, electricity is generated using a steam cycle only turbine instead of using steam and a portion of the syngas as a fuel in a combined cycle turbine. This allows the system to generate electricity without requiring the use of combustion, thereby eliminating the need for smokestacks and the release of environmental pollutants.

In this system, there are five primary locations of heat generated by exothermic reactions. These include: the MMBG 130; the Anaerobic Digester 140; the A/C Plasma Reactor 150; the Syngas Cleanup and Conditioning system 160; and the Product Recovery System 170 (depending upon the catalytic conversion process employed). For each of these locations or components 130, 140, 150, 160, 170, heat exchangers are installed to capture and transfer the generated heat from these locations. Thus, heat exchangers 210, 220, 230, 240 and 250 are attached or otherwise provided to 130, 140, 150, 160 and 170 respectively, as shown in FIG. 2. For each heat exchanger, a cool heat transfer medium (e.g., air; water; propylene glycol, etc.) 212, 222, 232, 242, and 252 is pumped from the Heat Recovery Steam Generation (HRSG) Utility 270 to each heat exchanger. The heat transfer media absorb heat from 130, 140, 150, 160 and 170 via the respective heat exchangers 210, 220, 230, 240 and 250 and are then cycled back to the HRSG 270 where the absorbed heat is used to convert water into pressurized steam. The pressurized steam generated 272 from the HRSG 270 is transferred to the Steam Turbine 280, which in turn generates electricity 282. The electricity is sent to a Power Conditioning System and Microgrid 290 where it is conditioned and redistributed 292 as conditioned electricity to power all of the system processes. The Power Conditioning System 290 is used to assure quality electric power with a standard voltage in order to meet the operating requirements of the equipment in the inventive system and/or the local utility (if excess electrical power is returned to the local utility power grid). The Microgrid provides a means to manage and distribute the generated electricity for use by the inventive system and its processes or to be returned to the local utility power grid. In addition, the Microgrid allows the inventive system to operate independently of utility grid power. Excess electricity (i.e., above plant load) may be used to create $H_2$ 296 and $O_2$ 298 through electrolysis in the Hydrogen and Oxygen Utility 294.

Exhaust steam 274 from the Steam Turbine 280 is recycled to the HRSG 270 for reheating. Similarly, excess steam/water vapor 262 is reheated by heat exchanger 260 and recycled 264 inside the HRSG 270. The regenerated pressurized steam 272 is returned to the Steam Turbine 280 to generate electricity.

In a preferred embodiment the heat recovery and steam generation process to generate electricity is net energy-positive (i.e., it produces more electricity than is required to power all of the processes throughout the system). Given the flexibility of the invention to adjust energy inputs (via the MMBG and the AD), there are many different ways this can be achieved. Following is but one example of how this can be achieved:

a. Assume an input of non-biodegradable feedstocks with an energy value of 8,600 BTU/lb at a rate of 25 TPH (tons per hour).

b. Assume an input of biodegradable feedstock at a rate of 75 TPH.
c. Assume the following:
   1. Gasification of one ton of non-biodegradables yields 30,000 scf of syngas.
   2. One ton of biodegradable feedstock in an anaerobic digester yields 4,842 scf of biogas.
d. Assume a high energy value of 340 BTU/scf of syngas.
e. Assume a high energy value of 750 BTU/scf of biogas.
f. Converting the unit of measure for the non-biodegradable feedstocks from BTU/pound to BTU/ton yields 17,200,000 BTU/ton (multiplying 8,600 BTU/lb×2000 [pounds/ton]). Therefore, at a rate of 25 TPH, the non-biodegradable feedstocks contain an energy value of 430,000,000 BTU/hour.
g. Multiplying the amount of biogas generated from the AD (4,842 scf/ton) times a rate of 75 tons per hour, yields 363,150 scf of biogas per hour. Multiplying this amount by the energy value of 750 BTU/scf yields 272,362,500 BTU/hour.
h. Therefore, energy inputs from all sources into the system yield 702,362,500 BTU/hour (BTU of non-biodegradables and the anaerobic digester).
i. The amount of process gas produced from non-biodegradables is 750,000 scf/hour (30,000 scf/ton at a rate of 25 TPH) and the amount of biogas produced by the anaerobic digester is 363,150 scf/hour (4,842 scf/ton at a rate of 75 TPH). Therefore, 1,113,150 scf of syngas is produced per hour by the system.
j. The energy value of the syngas is 378,471,000 BTU/hour (multiplying 1,113,150 scf/hour×340 BTU/scf).
k. Assume a high value requirement of 4,400,000 BTU/ton of non-biodegradable inputs to sustain the melt in the MMBG. Also assume this energy requirement represents 80% of the total energy used by all system processes. The energy needed to sustain the melt is 110,000,000 BTU/hour (4,400,000 BTU/ton×25 TPH).
l. The energy used by all processes (excluding the MMBG) is 27,500,000 BTU/hour (derived from the assumption that the energy needed to support the MMBG represents 80% of the total system processes).
m. As shown in item h above, the system generates 702,362,500 BTU/hour. Of this amount, the syngas product consumes 378,471,000 BTU/hour, and the MMBG consumes 110,000,000 BTU/hour, for a total of 488,471,000 BTU/hour. This leaves 213,891,500 BTU/hour for all other resources. Since all system processes excluding the MMBG require electricity, a conversion from BTU to KWH is appropriate.
n. Assuming radiant and other heat loss of 20%, the amount of energy lost equals 42,778,300 BTU/hour, leaving 171,113,200 BTU/hour available for heat recovery.
o. Assuming an 80% heat recovery efficiency, the amount of energy available to convert into electricity is 136,890,560 BTU/hour (multiplying the residual energy of 171,113,200 BTU/hour×0.80).
p. Assuming a low value power efficiency of 25% for the steam turbine, this yields 10,030 KW of electricity (Using a standard BTU to KW conversion of the 136,890,560 BTU/hour in item o above.).
q. The system resources, (excluding the MMBG), requires 8,060 KW (using the standard formula of 3,412 BTU per KW).
r. This results in a net positive of electricity generated of 1,970 KW for use in the creation of $H_2$ and $O_2$, for resale to local utilities, or other purposes.

Figure 3:
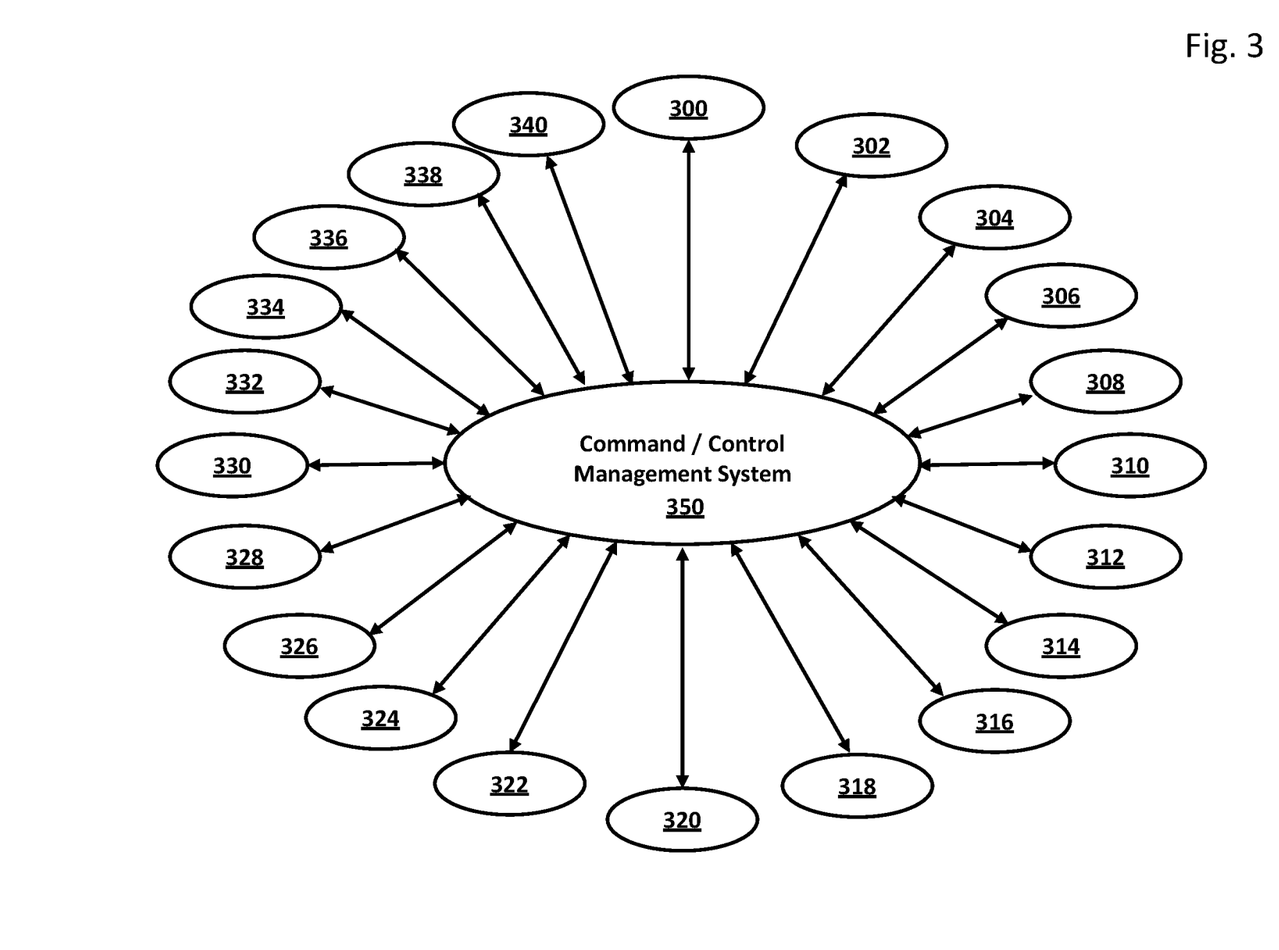
FIG. 3 is a flow diagram illustrating the preferred embodiment of the system for end-to-end monitoring and controlling each of the component processes, as well as the overall system.

Throughout this system, there are a minimum of 21 independent monitoring and control systems that collect data and manage local subsystem operations and one input system for feedstocks. These independent monitoring and control systems are comprised of myriad sensors that measure temperature, pressure, moisture, chemical composition, flow rates, weight, etc. Some systems check for mechanical jams, contain fire detection equipment and may include cameras to allow visual inspection of internal operations. Each of these monitoring and control systems is readily available in the marketplace and is provided for each major component sub-system. However, each monitoring and control system is designed for specific sub-system operations and not for monitoring or controlling the entire system end-to-end. For example, the Solids Processing Utility 112 has an independent monitor and control system 304 that measures and detects temperature, moisture, hose leaks, fires, equipment jams, etc., that are not shared with any other sub-processes in the system. Since downstream processes are dependent upon upstream processes for effective operation, it is imperative that an integrated system collects data from each subsystem, monitors all of the operations and allows for the management of the entire system and its components end-to-end. That integrated system is the Command/Control Management System (CCMS) 350 as shown in FIG. 3.

The CCMS 350 is an integrated system that collects data from all system processes, integrating them into one overarching monitor and control system, allowing end-to-end management of the entire process. The CCMS 350 collects data from each subsystem and displays them on a dashboard, allowing an operator to view the status and operation of one or more subsystems simultaneously. As shown in FIG. 3, these control and monitoring subsystems include, for example: feedstock type, composition and quantity 300; filtration of pumpable waste processes 302; solid non-pumpable, non-biodegradable waste processing 304; biodegradable waste processes 306; the anaerobic digester process (to include resource recovery) 308; effluent filtration processes 310; biogas filtration processing 312; the MMBG process (to include resource recovery) 314; the A/C plasma reactor process 316; syngas cleanup and conditioning processes 318; product recovery processes 320; the hydrogen/oxygen utility process 322; the MMBG heat exchanger process 324; the anaerobic digester heat exchanger process 326; the A/C plasma reactor heat exchanger process 328; the syngas cleanup and conditioning system heat exchanger process 330; the product recovery system heat exchanger process 332; the HRSG heat exchanger process 334; the HRSG processes 336; the steam turbine process 338; and the power conditioning system/microgrid processes 340. The CCMS 350 also allows for centralized remote access to any and all of these component subsystems to make adjustments in system processes as needed. It can also shut the entire facility down in the event of an emergency.

Thus, while fundamental novel features of the invention as applied to a preferred embodiment thereof have been described and pointed out, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for efficiently converting heterogeneous waste materials including biodegradable and/or non-biodegradable wastes into a high quality syngas, comprising:
    (a) receiving, by a molten metal bath gasifier (MMBG) having a molten metal bath, a non-biodegradable waste into the molten metal bath;
    (b) outputting by the MMBG a process gas from the non-biodegradable waste;
    (c) receiving, by an anaerobic digester disposed upstream from the MMBG, a biodegradable waste;
    (d) outputting by the anaerobic digester a biogas and effluent from the biodegradable waste; and
    (e) receiving and converting, by an alternating current (A/C) plasma reactor disposed downstream from the MMBG and the anaerobic digester, the process gas from the MMBG and the biogas from the anaerobic digester into a plasma phase and outputting raw syngas.

2. The method of claim 1, wherein the anaerobic digester is thermophilic operating at a temperature between about 49° C. and 57° C.

3. The method of claim 2, wherein the biogas from the thermophilic anaerobic digester has an average composition of 75% methane, 18% carbon dioxide, 1% nitrogen, 5% water vapor, 1% oxygen, and trace elements including hydrogen sulfide and ammonia.

4. The method of claim 1, wherein the anaerobic digester is mesophilic operating at a temperature between about 20° C. and 40° C.

5. The method of claim 4, wherein the biogas from the mesophilic anaerobic digester has an average composition of 65% methane, 28% carbon dioxide, 1% nitrogen, 5% water vapor, 1% oxygen, and trace elements including hydrogen sulfide and ammonia.

6. The method of claim 1, further comprising the step of positioning a plasma generator in the A/C plasma reactor to allow a plasma plume formed by the plasma generator to be oriented upward.

7. The method of claim 1, further comprising the step of excluding from the non-biodegradable wastes Universal Wastes defined in 40 CFR 273, explosives and munitions, radioactive materials, concentrated halogens and heavy metals.

8. The method of claim 1, further comprising the step of filtering and conditioning the outputted syngas from the A/C plasma reactor.

9. The method of claim 8, further comprising the step of converting the filtered and conditioned syngas into methanol and/or synthetic fuels.

10. The method of claim 1, further comprising the step of receiving by the MMBG the biogas from the anaerobic digester.

11. The method of claim 1, further comprising the step of receiving by the A/C plasma reactor a liquid from the non-biodegradable waste.

12. The method of claim 1, wherein the molten metal bath comprises iron.

13. The method of claim 1, wherein the non-biodegradable waste is pumpable, and further comprising the step of inputting the pumpable non-biodegradable waste into the MMBG and/or the A/C plasma reactor.

14. The method of claim 1, wherein step (e) does not emit any greenhouse gases or produce any residual landfill materials.

15. The method of claim 1, further comprising the step of providing a biogas filtration subsystem for filtering the biogas from the anaerobic digester for use as a working gas and/or process gas for the MMBG and/or the A/C plasma reactor, and an effluent filtration subsystem for filtering the effluent for use as a feedstock to the MMBG.

16. The method of claim 1, wherein the non-biodegradeable waste is pumpable and further comprising the step of filtering the pumpable non-biodegradeable waste.

17. The method of claim 1, wherein the non-biodegradeable waste is non-pumpable and further comprising the step of resizing the non-pumpable non-biodegradeable waste.

18. The method of claim 1, further comprising the step of resizing the biodegradable waste.

19. The method of claim 1, further comprising the step of recovering metals and/or minerals from a molten slag layer atop of the molten metal bath formed from dissociation of the non-biodegradable waste.

20. The method of claim 1, further comprising the steps of using induction heating to establish the molten metal bath and using heat generated from dissociation of the non-biodegradeable waste to maintain the molten metal bath.

21. The method of claim 1, further comprising the step of recovering water from the effluent produced by the anaerobic digester and feeding the recovered water into the molten metal bath of the MMBG and/or the anaerobic digester.

22. The method of claim 1, further comprising the step of monitoring quantity and type of the non-biodegradeable waste by tagging the non-biodegradeable waste with a unique identifier detectable by an electronic device.

23. The method of claim 22, wherein the unique identifier is one of barcode, quick response code, and radio frequency identification (RFID).

* * * * *